United States Patent [19]
Kalidindi

[11] Patent Number: 5,974,900
[45] Date of Patent: Nov. 2, 1999

[54] MANUALLY OPERATED STREAM SAMPLING DEVICE AND METHOD

[76] Inventor: Sanyasi R. Kalidindi, Globepharma, P.O. Box 10337, East Brunswick, N.J. 08906-9998

[21] Appl. No.: 09/022,045

[22] Filed: Feb. 11, 1998

[51] Int. Cl.[6] .................................................. G01N 1/26
[52] U.S. Cl. ...................... 73/863.57; 73/863.52
[58] Field of Search ............... 73/863.57, 863.52, 73/863.53, 864.63, 864.66

[56] References Cited

U.S. PATENT DOCUMENTS

| | | | |
|---|---|---|---|
| 2,526,298 | 10/1950 | Theonville | 73/863.52 X |
| 3,692,490 | 9/1972 | Hall | 73/864.62 X |
| 3,802,270 | 4/1974 | Daniels et al. | 73/863.52 |
| 4,433,587 | 2/1984 | Risdal | 73/863.54 |
| 4,663,978 | 5/1987 | Lenski et al. | 73/863.52 |
| 4,771,642 | 9/1988 | Parth et al. | 73/863.52 |
| 4,858,477 | 8/1989 | Wienck | 73/863.54 |
| 4,866,997 | 9/1989 | Kaufman | 73/864.63 |
| 5,471,886 | 12/1995 | Kalidindi | 73/864.63 |
| 5,476,017 | 12/1995 | Pinto et al. | 73/864.62 |
| 5,703,301 | 12/1997 | Pinto et al. | 73/864.63 |

FOREIGN PATENT DOCUMENTS

| | | | |
|---|---|---|---|
| 39-5897 | 4/1964 | Japan | 73/863.53 |
| 423845 | 9/1974 | U.S.S.R. | |

*Primary Examiner*—Thomas P. Noland
*Attorney, Agent, or Firm*—Richard C. Litman

[57] ABSTRACT

A sampling device for collecting unit dose, bulk or unit dose and bulk samples simultaneously at different periods from a falling stream of material directly into various sample containers. The sampling device enables the compressing of collected powder samples in the sampling cups directly with a compression machine without transferring the powder samples into another container. One size of the sampling device enables the sampling from different sized blenders, mixers and other containers. Multiple samples are obtained simultaneously. The sampling device is simple in construction, simple to use and simple to disassemble, clean and reassemble.

15 Claims, 3 Drawing Sheets

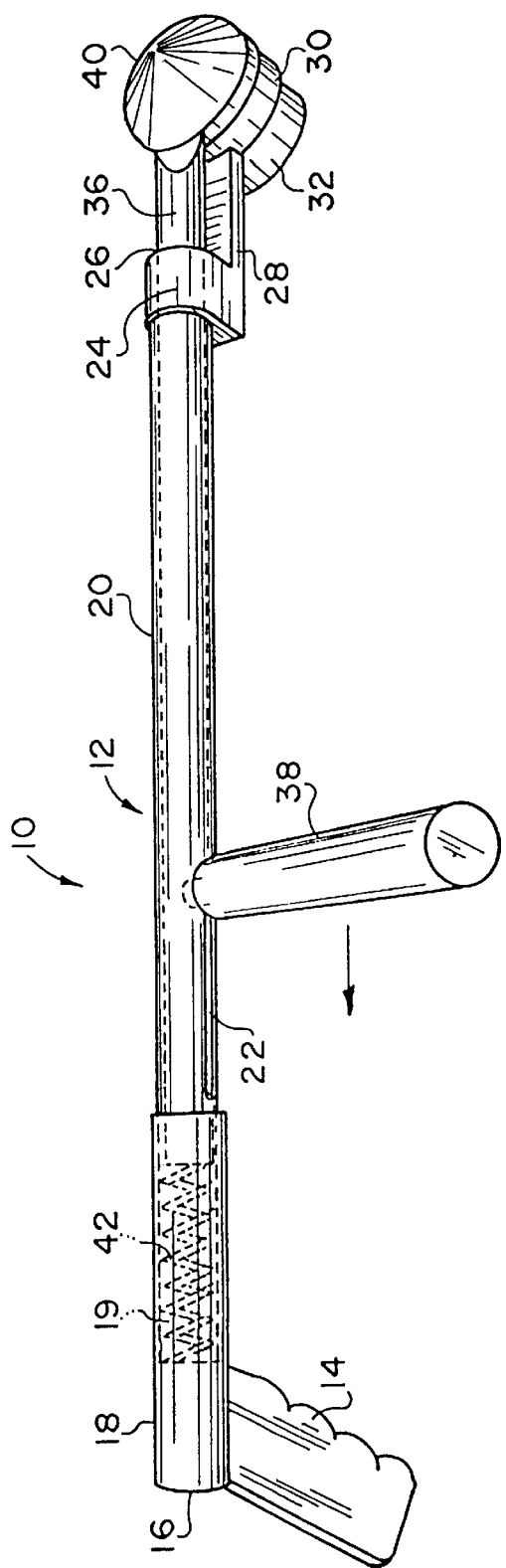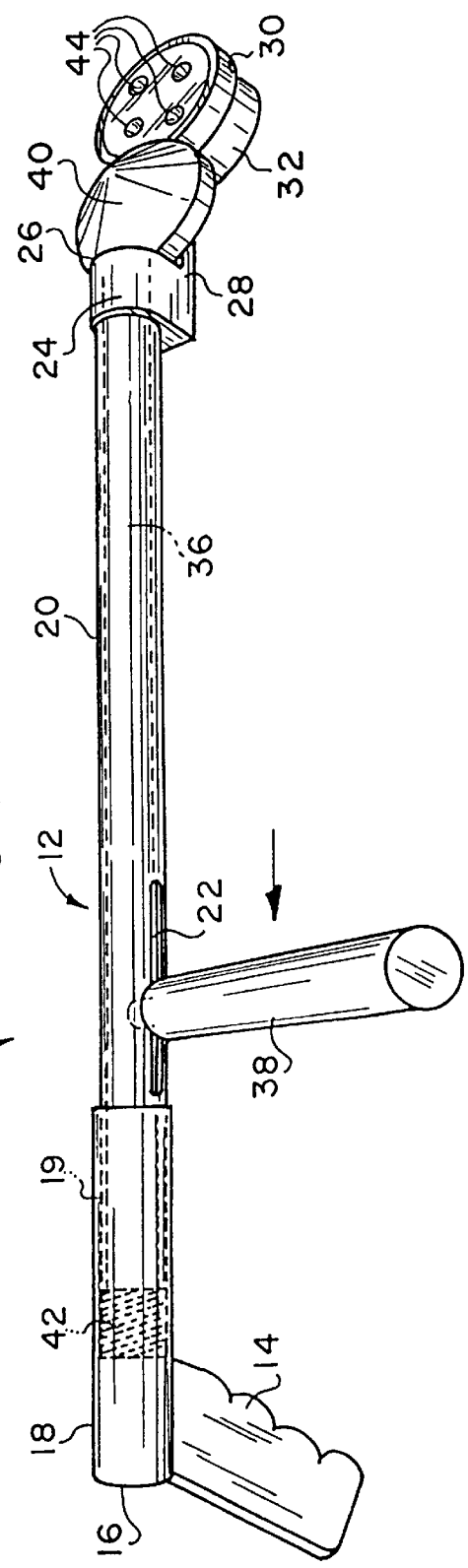

MANUALLY OPERATED STREAM SAMPLING DEVICE AND METHOD

BACKGROUND OF THE INVENTION

1. Field of the Invention

The present invention relates to a sampling device useful in taking unit dose samples and/or bulk samples of powders, liquids or semi-solids from a stream of pharmaceutical or food compositions at different time periods. Samples can be collected directly into gelatin capsules or any other suitable sample container positioned in the sampling device, thus eliminating the need to transfer the collected samples to sample containers. Alternatively, the samples can be collected into cavities in the sample collecting disc, and the samples subsequently compressed into pills using a compression machine.

2. Description of the Related Art

In the manufacture of solid dosage forms in the pharmaceutical and food industries, blending of different active and inactive ingredients is required in a blender. Such blends are routinely sampled and tested for uniformity in content. A proper sampling technique requires unit dose or bulk sampling from different areas of the blender, e.g., top, middle and bottom of the blender. A unit dose sample is defined as a sufficient sample size to provide one dose of the active ingredient. A bulk sample is defined as a sample size large enough to provide several doses of the active ingredient. Conventionally, samples are obtained by inserting a rod-shaped sampling device having multiple sampling cavities with or without dies into the blended composition undergoing mixing in a mixing vat, drum or the like. However, such a sampling technique, especially for powder compositions, disturbs a powder bed during sampling, thus influencing the test results, and requires samplers of different lengths for different depths. In addition, such powder sampling devices cannot offer the versatility of compressing the powder samples into tablets or collecting the powder samples directly into gelatin capsules. Moreover, conventional powder sampling devices do not combine unit dose and bulk sampling in one sampling device as in the present invention.

The related art will be discussed in the order of its perceived relevance to the present invention.

U.S. Pat. No. 5,476,017 issued on Dec. 19, 1995, to Ivan Pinto et al. describes a unit dose material sampling apparatus for removing a sample of granular or powder material from a vat in which such materials are mixed in bulk. A tubular housing contains a shaft with a piston on one end and a threaded section proximate the opposite end which has a thumb wheel and a spring outside the housing. The housing has a thumb or set screw which adjusts the volume of sample to be taken by cooperating with the threaded section of the shaft. The housing supports by external collars a cam rod and handle which rotates a conical closure cap for closing and opening the housing for sampling. The device is distinguished by its reliance on an internal piston structure to collect and pack the pharmaceutical powder sample.

Japan Patent No. 39-5897 issued on Apr. 28, 1964, describes an automatic sampler device for sampling a falling stream of a powder-grain mixture by mechanically inserting a cylindrical sampling tube into and withdrawing from the flowing stream. The sample mixture is mechanically dumped into a case. The device is distinguished by the dissimilar structure of the mechanical sampling device.

Russia Patent No. 423,845 issued on Sep. 4, 1972, describes an automatic sampling machine for obtaining single granules flowing down from a conveyor belt. The sampler consists of four truncated semicones on individual spokes of different adjustable lengths which rotate on a driven shaft in a ferris wheel manner. The intent is to sample granules from different parts of the falling stream. The rotating semicones dump their granules into a trough which feeds an analyzing device. The machine is distinguished by the mechanical and structural differences from the singular manual device of the present invention.

U.S. Pat. No. 4,771,642 issued on Sep. 20, 1988, to William H. Parth et al. describes two solids sampler devices (movable and non-movable) permanently positioned horizontally for collecting and continuously analyzing for moisture content by either infrared ray or neutron absorption of a sample of particulate polymer resin beads from a vertical pneumatic conveyer system pipe. The movable embodiment involves a sampling cup installed within the pipe with the sample collecting cavity moving in and out from below the cup. The devices are distinguished by their fixed structure.

U.S. Pat. No. 4,433,587 issued on Feb. 28, 1984, to Norton W. Risdal describes an automatic sampler device for dry material flowing under pressure of 15–100 p.s.i. in a horizontal flow duct or spout. The sampling device is attached at an oblique angle of 30–60° below the horizontal duct. The sample tube is housed in a tubular casing having an enlarged box chamber at an outer end connected to an air cylinder which controls the input and exhaust of pressurized air to motivate a piston to project a slotted sample tube into and out of the flow duct. The tubular casing has a sample delivery duct with a collection bag for automatically collecting the sample when the sample tube is retracted. The projection and retraction periods are automated by timers. The dry material sampling device is distinguished by its fixed and automatic structure of the dry material sampler.

U.S. Pat. No. 4,858,477 issued on Aug. 22, 1989, to Dennis A. Wienck describes an improved dry material sample collector for intermittently sampling a cross-section of a conveyed bulk material such as a cement mixture. A permanently housed sampling unit is affixed on a liquid cement mixture flow pipe with its collector head, i.e., a hollow piston rod, inserted in the cement flow. The housing contains a pneumatic cylinder and various flow control valves such as a check valve, a pinch valve, a long delay switch valve, and a short delay adjustment switch modular valve. The liquid cement mixture is separated within the housing to collect the sample in a jar and to exhaust gas. The dry material sample collector is distinguished by its dissimilar structure.

U.S. Pat. No. 4,663,978 issued on May 12, 1987, to Ralph Linski et al. describes a clean grain sampler for a combine harvester. A prism-shaped receiving cup rocks about its bottom edge to collect grain samples and dumps the samples with its sides acting as closures for the grain tank. The clean grain sampler is distinguished by its unique pivoting structure.

U.S. Pat. No. 4,866,997 issued on Sep. 19, 1989, to Kevin W. Kaufman describes a telescopic grain probe with a thermistor attached at one end to automatically measure the temperature of the grain sample. The probe tip has a grain receiving chamber which is automatically closed on insertion of the probe device, and automatically opened for sampling by two diametrically opposed inclined fins which accommodate flaps. The structural differences of the temperature measuring grain probe distinguish this apparatus from the present invention.

None of the above inventions and patents, taken either singularly or in combination, is seen to describe the instant invention as claimed. Thus, the manually operated stream sampling device solving the aforementioned problems is desired.

SUMMARY OF THE INVENTION

The present invention is a hand operated sampling device and a method for obtaining samples from a falling stream of pharmaceutical or food compositions in the form of powders, liquids or semi-solids. The present invention consists of two concentric cylindrical tubes. The outer tube is closed at one end with a vertically disposed grip handle. A bracketed ring is attached to its opposite end. The ring can accommodate a cup with cavities, empty gelatin capsules or an adapter with a bottle to collect samples. The inner tube is sealed at both ends, has a horizontally disposed handle at one end and a conical cover for the sampling cup at the other end. This inner tube nests inside the outer tube and abuts a spring. The outer tube has a slot so that the handle on the inner tube can be moved back to open the sampling cup and forward to close the cup. The sampling cup can be fabricated as one piece having cavities for accommodating the empty gelatin capsules, or it can be fabricated as a two-section unit with both sections fastened together by screws. The upper section has a plurality of cavities for collecting powder, whereas the lower section is a blank disc. Such a two-section construction allows the collected powder samples to be compressed into pills. In addition, the thickness of the upper section can be varied in order to alter the size of each sample collected.

The procedure for collecting samples involves holding the sampling device by the grip handle out into the material stream. When sampling, the horizontal handle is pulled back to open the sampling cup and compressing the spring. When the sampling cavities are filled, the handle is released to cover the cup automatically and to scrape off any excess sample as the compressed spring expands. If the samples are collected in gelatin capsules, the capsule bodies with samples are ejected out slightly from the sampling cup, capped and ejected from the cup. If the sample is collected into a bottle, then the bottle is removed from the adapter in the ring and capped. If the samples are collected directly into cavities, then the samples can be compressed into pills by a tablet compression machine.

Thus, the invention addresses the previously mentioned problems by offering the following advantageous features: (1) One size sampler covers any blender vessel size. (2) Unit dose sampling and/or bulk sampling accomplished at different time periods. (3) No disturbance of the powder bed during sampling. (4) Sample is collected directly into gelatin capsules. (5) Compression of powder samples without transference of the samples to another container. (6) Simplicity of design and the ease of use, cleaning and assembling of the sampling device.

Accordingly, it is a principal object of the invention to provide a hand operated device and a method for sampling falling material streams.

It is another object of the invention to provide a hand operated stream sampling device which includes a conical cover over the sampling cup which is opened and closed with spring action.

It is a further object of the invention to provide a hand operated stream sampling device including two handles, wherein one handle for extending the device into the composition stream and the other handle for removing and replacing the cover over the sampling cup.

Still another object of the invention is to provide a hand operated stream sampling device which offers the versatility of utilizing different sampling cups for collecting unit dose samples into capsules, bulk samples into bottles, and unit dose powder samples which can be compressed into tablets.

It is an object of the invention to provide improved elements and arrangements thereof in a hand operated stream sampling device for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a perspective view of a hand operated material stream sampling device before sampling according to the present invention.

FIG. 2 is a perspective view of the FIG. 1 sampling device uncovered for sampling.

Similar reference characters denote corresponding features consistently throughout the attached drawings.

DETAILED DESCRIPTION OF THE PREFERRED EMBODIMENTS

Figure 3:
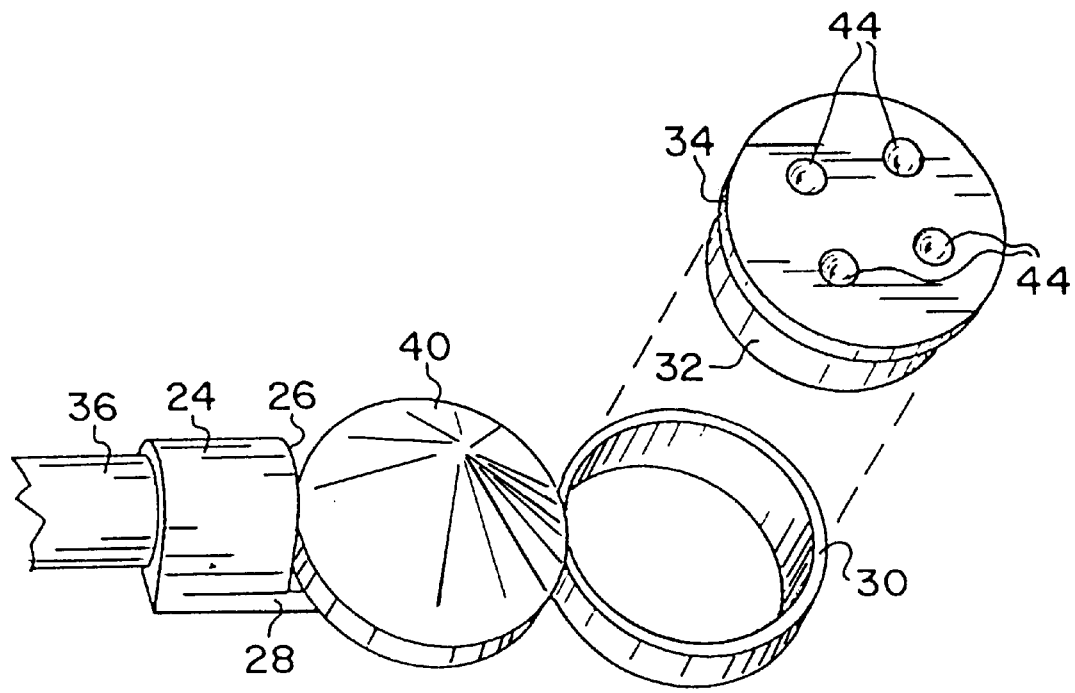
FIG. 3 is a partial exploded perspective view of the distal end of the FIG. 2 sampling device with a single component sampling cup for non-pilling purposes.

The present invention provides a device for manually sampling of materials from a falling production stream. In FIGS. 1 and 2, a manually operated powder stream sampling device 10 is depicted before sampling and during sampling, respectively. The device 10 has an elongated cylindrical metal casing 12, preferably made of stainless steel, having a first vertical plastic grip handle 14 at a proximate end 16 of the casing 12. The pistol grip handle 14 is attached to a partially solid metal sleeve 18 having a blind bore 19 which is contiguous to a tubular portion 20 of the casing element 12. A slot 22 along the horizontal axis of the tubular portion 20 is present adjacent to the sleeve 18.

A metal elbow bracket 24, preferably made of stainless steel, is welded at the distal end 26 of the contiguous tubular portion 20 and casing 12. The bracket 24 includes a tongue portion 28 and a cup holding ring 30 underneath and along the longitudinal axis of the tubular portion 20. A cylindrical metal (preferably stainless steel) or a plastic sampling cup 32 having a flange or lip 34 for obtaining multiple powder samples is supported by the ring 30. It should be noted that the bracket 24, the cup 32 and the grip handle 14 are in axial alignment.

A sealed cylindrical metal tube 36, preferably made of stainless steel, is adapted to slide within the tubular portion 20. The tube 36 has a second plastic cylindrical handle 38 at a proximate end and a conical cover element 40 at a distal end. The removable handle 38, threadably connected to the tube 36, is both dimensioned and configured to slide in the slot 22 of the tubular portion 20. The tube 36 is pressured forward by an attached metal compression spring 42 (shown in shadow) which abuts the sleeve 18 at its opposite end to maintain the cover element 40 over the sampling cup 32.

It should be noted that the compression spring 42 is never exposed because it is confined within the sleeve 18, thus preventing any contamination of the samples by the spring 42. Cleaning of the sampling device 10 after use is simplified because of the ease with which the sampling device 10 can be dismantled. Once the handle 38 is removed by unthreading, the casing 12 with its appended elbow bracket 24 and the tube 36 with compression spring 42 and its appended cover element 40 are easily separated by sliding out the tube 36.

The second pull handle 38 is offset by an angle of 90° from (or perpendicular to) the pistol grip handle 14. Although the second handle 38 is shown as offset for a right-handed user, the slot 22 and the handle 38 can be positioned on the opposite side of the casing 12, if preferred, for a left-handed user. The arrows in FIGS. 1 and 2 show the direction of pulling the handle 38 to uncover the sampling cup 32.

In FIG. 3, the pull handle 38 has been pulled back and held to remove the cover element 40 to expose the sampling cup 32 which in this example is one-piece for sampling into capsules. An exemplary number of four cavities 44 containing open plastic capsule bodies (not shown) in the sampling cup 32 is depicted, but it should be understood that any number of cavities 44 can be accommodated according to the space available and the size of each capsule. The sampling cups 32 can be plastic or metal.

Figure 4:
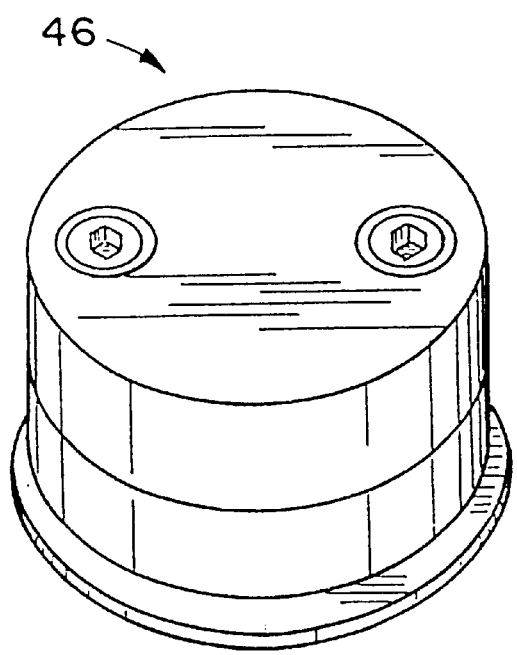
FIG. 4 is a perspective bottom view of a sampling cup with two sections for allowing the compression of the powder sample into tablets.

In FIG. 4, a two-section metal sampling cup 46, preferably made of tool steel, is shown inverted. for obtaining samples for pilling purposes is shown inverted. This cup is used for obtaining powder samples which can be separately compressed into tablets. The cup 46 has a top portion 48 (bottom portion in the drawing) and a bottom portion 50 with two fasteners 52 having Allen wrench sockets for fastening the cup portions 48, 50 together.

Figure 5:
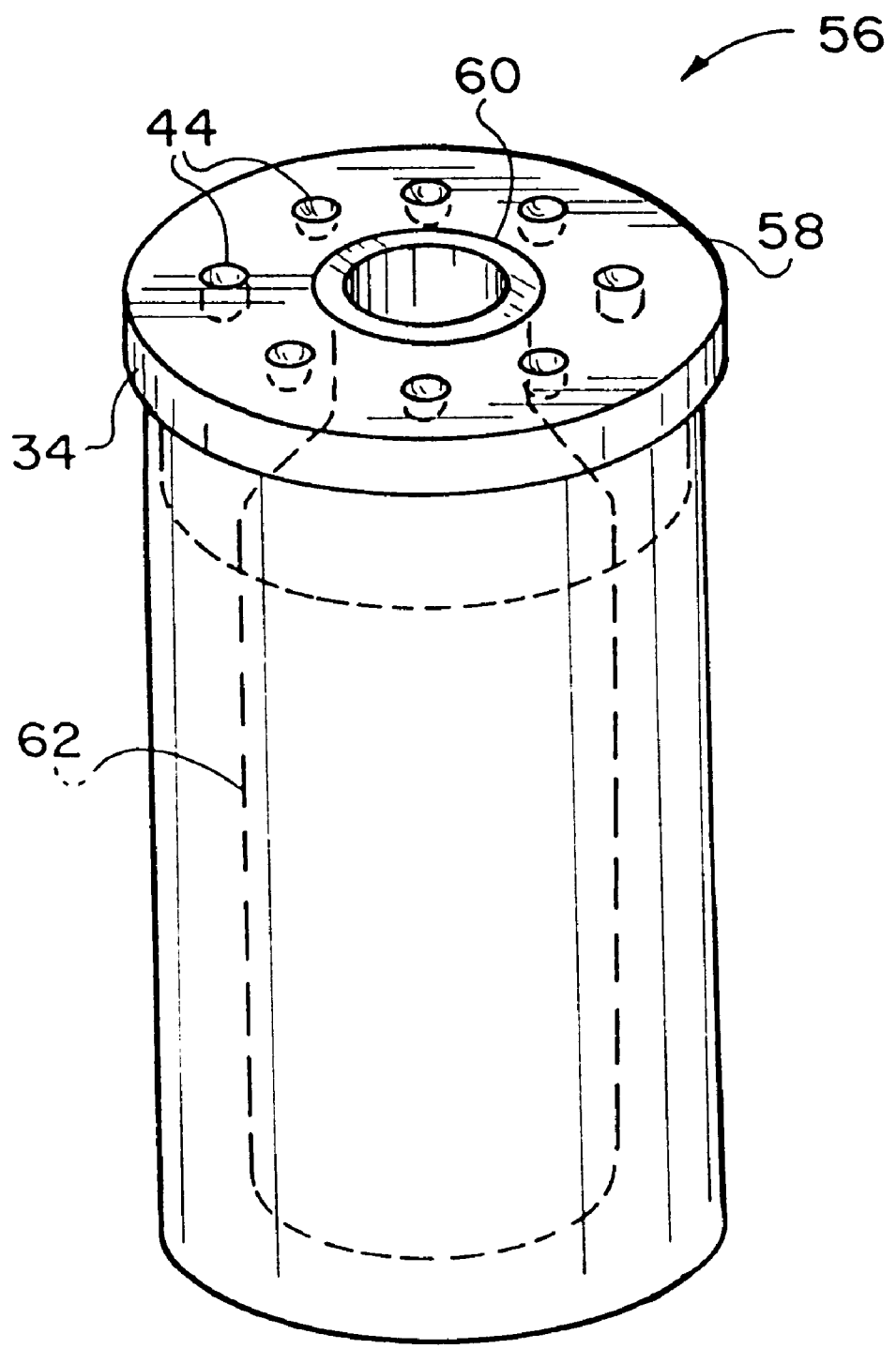
FIG. 5 is a perspective side view of a sampling cup with a bottle in the center surrounded by cavities on a top surface.

In FIG. 5, another sampling cup 56 is shown. The cup 56 has a plastic adapter 58 with a threaded bore 60 in the center for a sampling bottle 62 to be threaded in. The flange 34 on the adapter 58 fits on the ring 30 of the sampling device 10. The adapter also has cavities 44 on the periphery for allowing simultaneous unit dose as well as bulk sampling.

As shown in FIGS. 3, 4 and 5, cups 32, 46 and 56, respectively, have a collar or flange 34 for abutting the cup holding ring 30. The sampling device 10 must be dimensioned to precisely permit the cover element 40 to slide back over the sampling cups 32, 46 and 56 to scrape off any excess powder.

The method of sampling by utilizing the sampling device 10 begins by inserting the sampling device 10 into a material stream and sliding back the cover element 40 by pulling back the second handle 38 to expose the sampling cup 32, 46 or 46 to collect samples and then covering the sample cup 32, 46 or 56 by releasing the handle 38 which is pushed forward by the released spring 42. Then the samples are removed according to the following situations.

(1) If the sampling cup 32 is used, then the capsule bodies are partially ejected first from the cavities 44 by pushing the capsule bodies up from underneath the sampling cup 32 by using a plastic ejection tool with an appropriate number of pins (not shown), locking the caps on the capsules, and then removing the closed capsules from the sampling cup 32.

(2) If the sampling cup 46 is used, then the powder samples in the cavities 44 are compressed into pills using a separate compression machine, the bottom section 50 is separated from the top section 48 by removing the fasteners 52 in the bottom 54 of the cup 46, and ejecting the pills from the top section 48 using the same compression machine.

(3) If the sampling cup 56 is used, the bottle 62 with the bulk sample is removed by unscrewing the bottle from the adapter 58, and the capsules in the cavities 44 are removed as described in (1).

It is to be understood that the present invention is not limited to the embodiments described above, but encompasses any and all embodiments within the scope of the following claims.

I claim:

1. A hand operated sampling device for sampling a falling material stream comprising:

(a) an elongated cylindrical casing having a proximate end and a distal end, and comprising:
  (1) a partially solid sleeve portion at said proximate end of said casing, said sleeve portion containing a blind bore,
  (2) a first handle attached to said partially solid sleeve portion at said proximate end of said casing,
  (3) a tubular portion abutting said partially solid sleeve portion and extending to said distal end of said casing,
  (4) a slot in said casing proximate to said blind bore, and
  (5) an elbow bracket supporting a tongue portion connected to a ring, (b) a cylindrical tube having a proximate end and a distal end, and adapted to slidably extend from within said casing and through said elbow bracket, comprising:
  (1) a second handle positioned at the proximate end of said tube and slidably positioned in said slot of said casing; and
  (2) a cover element attached to said distal end of said tube;

(c) a sampling cup containing a plurality of sampling cavities, said cup being removably contained by said ring of said bracket;
  whereby a sample is obtained by inserting said sampler device into a falling material stream, and sliding back said cover to collect a sample and then covering said sampling cup.

2. The sampling device according to claim 1, wherein said falling material stream is selected from the group consisting of powder, liquids and semi-solids.

3. The sampling device according to claim 1, wherein said sampling cavities contain open gelatin capsules.

4. The sampling device according to claim 1, wherein said first handle being aligned with said sampling cup.

5. The sampling device according to claim 4, wherein said first handle being a pistol grip.

6. The sampling device according to claim 1, wherein said second handle being removably threaded to said slidable cylindrical rod for dismantling said sampling device for cleaning.

7. The sampling device according to claim 1, wherein said second handle being positioned at an offset angle of 90° to said first handle and perpendicularly to said slidable cylindrical rod.

8. The sampling device according to claim 7, wherein said second handle being removable, cylindrical and offset for a right-handed user.

9. The sampling device according to claim 1, wherein said sampling cup being of one-piece construction for obtaining samples in open capsules in said cavities.

10. The sampling device according to claim 1, wherein said sampling cup being of two-piece construction for obtaining samples in a plurality of cavities for subsequent compression into tablets.

11. The sampling device according to claim 1, wherein said sampling cup having a plastic adapter to accommodate a sampling bottle and having said cavities on the periphery for collecting samples for open capsules.

12. The sampling device according to claim 1, wherein said sampling cup having a plurality of cavities for multiple samples.

13. The sampling according to claim 1, wherein said cover element being conical in shape for shedding a material stream containing powder.

14. The sampling device according to claim 1, wherein said cover element being dimensioned, configured and positioned to scrape off excess powder when concluding the sampling procedure.

15. The sampler device according to claim 1, a spring being located within said casing in the region of said slot for pressing said cylindrical rod and said cover forward to cover said sampling cup.

* * * * *